US007112613B2

(12) United States Patent
Gamlin et al.

(10) Patent No.: US 7,112,613 B2
(45) Date of Patent: Sep. 26, 2006

(54) PROCESS FOR SEPARATING LIQUID HYDROCARBONS FROM A PARTICULATE FISHER-TROPSCH CATALYST

(75) Inventors: Timothy Douglas Gamlin, Woking (GB); Carole Graham, Edinburgh (GB); John Richard Hensman, Letchworth (GB); Barry Nay, Woking (GB); David Newton, Farnham (GB)

(73) Assignees: BP Exploration Operating Company Limited, London (GB); Davy Process Technology Limited, London (GB)

( * ) Notice: Subject to any disclaimer, the term of this patent is extended or adjusted under 35 U.S.C. 154(b) by 0 days.

(21) Appl. No.: 10/476,623

(22) PCT Filed: May 17, 2002

(86) PCT No.: PCT/GB02/02337

§ 371 (c)(1),
(2), (4) Date: Nov. 3, 2003

(87) PCT Pub. No.: WO02/096840

PCT Pub. Date: Dec. 5, 2002

(65) Prior Publication Data

US 2004/0132835 A1 Jul. 8, 2004

(30) Foreign Application Priority Data

May 25, 2001 (GB) ................................ 0112806.5

(51) Int. Cl.
*C07C 27/00* (2006.01)

(52) U.S. Cl. ....................... 518/700; 518/705; 518/712

(58) Field of Classification Search ................ 518/700, 518/705, 712

See application file for complete search history.

(56) References Cited

U.S. PATENT DOCUMENTS

| | | | |
|---|---|---|---|
| 4,306,970 | A | 12/1981 | Tanaka et al. |
| 4,605,678 | A | 8/1986 | Brennan et al |
| 5,036,365 | A | 7/1991 | Landa |
| 5,422,375 | A | 6/1995 | Rytter et al. |
| 5,961,933 | A | 10/1999 | Casanave et al. |

FOREIGN PATENT DOCUMENTS

| | | | |
|---|---|---|---|
| DE | 3245318 | A1 | 6/1984 |
| DE | 263 466 | A | 1/1989 |
| GB | 728543 | A | 4/1955 |
| WO | WO 01 38269 | A | 5/2001 |

*Primary Examiner*—J. Parsa
(74) *Attorney, Agent, or Firm*—Nixon & Vanderhye

(57) ABSTRACT

Process for converting synthesis gas to hydrocarbons which comprises contacting a gaseous stream comprising synthesis gas, at an elevated temperature and pressure, with a suspension comprising a particulate Fischer-Tropsch catalyst having a particle size in the range 5 microns to 500 microns, suspended in a liquid medium, in a system comprising at least one high shear mixing zone and a reactor vessel. The suspension and the gaseous stream is passed through the high shear mixing zone(s) wherein the gaseous stream is broken down into gas bubbles. The suspension having gas bubbles dispersed therein is discharged from the high shear mixing zone(s) into the reactor vessel, and suspension comprising the particulate Fischer-Tropsch catalyst suspended in the liquid medium and liquid hydrocarbon products is withdrawn from the reactor vessel and at least a portion of the suspension is recycled to the high shear mixing zone(s) via an external conduit at a flow rate of at least 10,000 $m^3$ of suspension per hour. A side stream from the suspension flowing through the external conduit is taken and passed directly to a filtration unit.

18 Claims, 4 Drawing Sheets

PROCESS FOR SEPARATING LIQUID HYDROCARBONS FROM A PARTICULATE FISHER-TROPSCH CATALYST

This application is the U.S. National Phase of International Application PCT/GB02/02337, filed May 17, 2002, which designated the U.S.

BACKGROUND OF THE INVENTION

The present invention relates to a process for the separation of liquid hydrocarbons from a particulate Fischer-Tropsch catalyst.

In the Fischer-Tropsch reaction a gaseous mixture of carbon monoxide and hydrogen (synthesis gas) is reacted in the presence of a catalyst to give a hydrocarbon mixture having a relatively broad molecular weight distribution. This product is predominantly straight chain, saturated liquid hydrocarbons which typically have a chain length of more than 5 carbon atoms. Fischer-Tropsch processes may be operated using slurry systems which employ a suspension of catalyst particles in a liquid medium. In a slurry process it is necessary to separate the liquid hydrocarbon products of the Fischer-Tropsch synthesis reaction from the Fischer-Tropsch catalyst.

PCT patent application number WO 98/50492 relates to a process for filtering hydrocarbon liquid from a three phase hydrocarbon slurry comprising gas bubbles and particulate catalyst solids in a hydrocarbon liquid, wherein the slurry is fed through a hydrocarbon liquid filtration zone by means of a gas disengaging downcomer immersed in the slurry, so that it contacts the filter under flow conditions. The gas disengaging downcomer produces a gas reduced, densified slurry and passes it to a filtration zone either inside or outside the slurry reactor. The gas reduced and densified slurry flows past and contacts the filter under relatively high net flow conditions in a net single direction as filtration occurs. This is said to reduce the buildup of catalyst particles as filter cake on the filtration surface of the filter, due to the shearing, scouring and removing action of the flowing slurry. The process of WO 98/50492 relies on a difference in density between the gas reduced slurry and the slurry body in the reactor to circulate slurry through the filtration zone. It has now been discovered that it is possible to feed slurry through a filtration unit by means of a mechanical pump, for example, an impeller, propeller or the like. This is surprising since WO 98/50492 teaches against using mechanical means, because they will quickly erode and cause attrition of the catalyst particles. Furthermore, the process of the present invention allows the suspension to be filtered without first having to reduce the gas content of the slurry.

SUMMARY OF THE INVENTION

It has now been found that liquid hydrocarbons may be separated from a slurry having gas bubbles and/or irregularly shaped gas voids dispersed therein by passing the slurry through a filtration unit comprising a conventional filter element, above a minimum flow rate wherein the slurry is circulated through the filtration unit via a mechanical pumping means. It has also been found a stream having a reduced content of particulate Fischer-Tropsch catalyst may be separated from a stream having an increased content of particulate Fischer-Tropsch catalyst in a filtration unit comprising a T-piece magnetic separator wherein the slurry having gas bubbles and/or irregularly shaped gas voids dispersed therein is passed to the T-piece magnetic separator via a mechanical pumping means.

Thus, the present invention provides a process for filtering a suspension comprising a particulate Fischer-Tropsch catalyst suspended in liquid hydrocarbons and having synthesis gas dispersed therein in the form of gas bubbles and/or irregularly shaped gas voids which process comprises:

passing the suspension through a filtration unit via a mechanical pumping means under turbulent flow conditions.

The filtration unit may comprise a conventional filter element or may comprise a T-piece magnetic separator.

Where the filtration unit comprises a conventional filter element, liquid hydrocarbons are separated from the suspension. Where the filtration unit comprises a T-piece separator, a stream having a reduced content of particulate Fischer Tropsch catalyst is separated from a stream having an increased content of particulate Fischer-Tropsch catalyst.

The suspension is passed through the filtration unit under turbulent flow conditions. Suitably, the Reynolds number of the suspension passing through the filtration unit is in the range 0.2 to 120.

Where the filtration unit comprises a conventional filter element, the suspension is preferably passed through the filtration unit at a flow rate of at least 2,500 $m^3$ of suspension per hour. Without wishing to be bound by any theory it is believed that when the suspension is passed through the filtration unit at a flow rate of at least 2,500 $m^3$ of suspension per hour, that there is no requirement to separate larger catalyst particles from the suspension before introducing the suspension to the filtration unit. Suitably, the suspension is passed through the filtration unit at a flow rate of at least 5,000 $m^3$ of suspension per hour, preferably at a flow rate of from 10,000 to 50,000 $m^3$ of suspension per hour, more preferably 15,000 to 30,000 $m^3$ of suspension per hour, most preferably 17,000 to 25,000 $m^3$ of suspension per hour.

Suitably, the liquid hydrocarbons may be separated from the particulate Fischer-Tropsch catalyst, by applying a pressure differential across the filter element in the filtration unit, so that at least a portion of the liquid hydrocarbons permeate through the filter element ("filtrate stream") and a concentrated suspension of particulate catalyst in the liquid hydrocarbons is retained by the filter element ("retentate stream"). Typically, the pressure differential across the filter element is at least 0.05 bar, preferably 0.05 to 30 bar, more preferably 0.05 to 10 bar, most preferably 0.05 to 3 bar, for example, 0.05 to 1 bar. Preferably, the pressure of the suspension passed through the filtration unit(s) is greater than the pressure on the filtrate side of the filter element(s) which in turn is greater than the pressure of the filtrate stream removed from the filtration unit thereby maintaining the flow of the filtrate stream through the filter element(s).

Preferably, the flow rate of suspension across the surface of the filter element is at least 1 $ms^{-1}$, more preferably at least 3 $ms^{31\ 1}$.

Preferably the flux (which for the purposes of this patent is defined as the volume of filtrate permeating through the filter element per second through 1 $m^2$ of filtration area) is at least 5 $l/m^2/s$, preferably at least 10 $l/m^2/s$, more preferably in the range 10 to 50 $l/m^2/s$.

Suitably, the retentate stream comprises a concentrated suspension of the particulate Fischer-Tropsch catalyst in the liquid hydrocarbons. Preferably, the ratio of the amount of liquid hydrocarbons which permeates through the filter element (filtrate stream) to the amount of liquid hydrocarbons which is retained in the retentate stream may be in the range 0.1:100 to 60:100. Preferably, the concentrated suspension comprises at least 50% wt of catalyst particles, more preferably, at least 60% wt of catalyst particles.

Suitably, the catalyst is maintained in suspension in the retentate stream so as to mitigate the risk of a filter 'cake' being formed on the surface of the filter element. A further advantage of maintaining the catalyst in suspension in the retentate stream is that the retentate stream may be recycled from the filtration unit to a Fischer-Tropsch synthesis reactor.

In order to prevent any build up of catalyst particles on the surface of the filter element the differential pressure across the filter element may be periodically removed or the filter element may be periodically back-flushed with liquid hydrocarbons.

Suitably, the system may comprise a plurality of filtration units, preferably, 2 to 5 filtration units, for example 2 to 4 filtration units. Preferably, the plurality of filtration units are arranged in parallel. It is envisaged that a portion of suspension may be passed through each of the filtration units. However, it is preferred that at least one of the filtration units is redundant i.e. is only brought into operation when it is necessary to clean the filter element in a filtration unit.

Preferably, the filtration unit(s) comprises a plurality of filter elements, for example, at least 5, preferably at least 10 filter elements.

The filter element(s) is porous and has pore sizes which are small enough to prevent passage of the particulate catalyst Fischer-Tropsch catalyst through the filter element. Typically the pore size is less than the size of the smallest catalyst particles, preferably the pore size is substantially less than the size of the smallest catalyst particles (in order to avoid plugging of the pores with catalyst particles).

The filter element(s) of the present invention may be made of any suitable material which is resistant to the liquid hydrocarbons, for example, sintered metal, ceramic materials, polymeric materials. A preferred filter material is sintered metal. The filter element(s) may be flat, tubular (including circular, square, rectangular, triangular cross section), or spiral wound. Where the filter element(s) is tubular, the element(s) is preferably aligned with the longitudinal axis of the filtration unit.

The filtration unit may be operated with a headspace into which any entrained gases (gas bubbles and/or irregularly shaped gas voids) and dissolved gases separate from the suspension. Preferably, the volume of the headspace is not more than 25%, more preferably not more than 10% of the volume of the filtration unit. However, it is also envisaged that the filtration unit may be operated in the absence of a headspace provided that the gas bubbles and/or irregularly shaped gas voids remain dispersed within the suspension as the suspension is passed through the filtration unit.

As discussed above, a stream having a reduced content of particulate Fischer-Tropsch catalyst may be separated from a stream having an increased content of particulate Fischer-Tropsch catalyst in a filtration unit comprising a T-piece magnetic separator. This T-piece magnetic separator comprises a main conduit and at least one branch conduit. Suitably, magnetic devices are disposed on the main conduit in the vicinity of the branch conduit(s). Suspension is passed through the main conduit of the T-piece magnetic separator and a stream having a reduced content of particulate Fischer-Tropsch catalyst is removed from the branch conduit(s). The magnetic devices assist in retaining the particulate Fischer-Tropsch catalyst within the main conduit. Suspension having an increased content of Fischer-Tropsch catalyst is removed from the main conduit downstream of the branch conduit(s). Suitably, the stream which is withdrawn from the branch conduit(s) is reduced in catalyst content by at least 10%, preferably at least 20%, more preferably at least 30%, most preferably at least 40%, for example, at least 50% relative to the suspension stream which is passed to the T-piece magnetic separator. Suitably, the stream having a reduced content of Fischer-Tropsch catalyst is introduced into the main conduit of a further T-piece magnetic separator. Preferably 2 to 4 T-piece magnetic separators are connected in series. The stream having a reduced solids content which is withdrawn from the last separator in the series is preferably passed to a conventional filter where the liquid hydrocarbons and any liquid medium may be separated from any remaining particulate Fischer-Tropsch catalyst by applying a pressure differential across the filter element. Preferably, the stream having an increased content of particulate Fischer-Tropsch catalyst is recycled back to the reactor as a concentrated slurry.

Where the filtration unit comprises a T-piece magnetic separator, the suspension is preferably passed through the separator at a flow rate of at least 1,000 $m^3$ of suspension per hour, preferably at least 2,000 $m^3$ of suspension per hour, more preferably at least 5,000 $m^3$ of suspension per hour, for example, at least 10,000 $m^3$ of suspension per hour.

In yet a further aspect of the present invention there is provided a T-piece magnetic separator comprising a main conduit having at least one branch conduit and having magnetic devices disposed on the outer surface of the main conduit, in the vicinity of the branch conduit(s).

In a preferred embodiment of the present invention, there is provided a process for converting synthesis gas to hydrocarbons, at least a portion of which are liquid at ambient temperature and pressure, which comprises contacting synthesis gas, at an elevated temperature and pressure, with a suspension comprising a particulate Fischer-Tropsch catalyst suspended in a liquid medium, in a reactor system comprising at least one high shear mixing zone and a tank reactor wherein the process comprises:

a) passing the suspension and synthesis gas through the high shear mixing zone(s) wherein the synthesis gas is broken down into gas bubbles and/or irregularly shaped gas voids;
b) discharging suspension having gas bubbles and/or irregularly shaped gas voids dispersed therein from the high shear mixing zone(s) into the tank reactor;
c) withdrawing a suspension stream comprising the particulate Fischer-Tropsch catalyst suspended in the liquid medium and liquid hydrocarbons from the tank reactor wherein the withdrawn suspension stream has gas bubbles and/or irregularly shaped gas voids dispersed therein;
d) passing at least a portion of the withdrawn suspension stream through at least one filtration unit via a mechanical pumping means under turbulent flow conditions;
e) withdrawing a filtrate stream comprising the liquid medium and liquid hydrocarbons from the filtration unit(s); and
f) recycling a retentate stream comprising a concentrated suspension of the particulate Fischer-Tropsch catalyst suspended in the liquid medium and liquid hydrocarbons from the filtration unit(s) to at least one of (i) the high shear mixing zone(s), (ii) the tank reactor, (iii) the suction side of a venturi nozzle and (iv) the withdrawn suspension stream.

In order to simplify the process of the preferred embodiment of the present invention it is preferred that the liquid medium comprises one of more of the liquid hydrocarbons.

Suitably, the filtration unit(s) may be positioned on an external conduit having a first end in communication with the tank reactor and a second end in communication with the high shear mixing zone(s). In this arrangement, the mechanical pumping means, for example, a slurry pump, is positioned in the external conduit upstream of the filtration unit(s). An external heat exchanger may be positioned on the external conduit, preferably, downstream of the mechanical pumping means, so as to assist in removing exothermic heat of reaction from the reactor system. The heat exchanger may be located either upstream or downstream of the filtration unit(s), preferably downstream. Where two or more filtration units are employed, it is preferred that these are arranged in parallel on the external conduit, optionally, with one or more redundant filtration units, as described above. The filtrate stream is withdrawn from the filtration unit(s) and may be passed to product purification and upgrading stages as described in WO 0138269 (PCT patent application number GB 0004444) which is herein incorporated by reference. Preferably, the entire retentate stream from the filtration unit(s) is recycled to the high shear mixing zone(s) via the external conduit. However, where the pressure of the retentate stream ($P_{retentate}$) is higher than the pressure in the tank reactor ($P_{reactor}$), it is envisaged that a retentate side stream may be taken from the external conduit downstream of the filtration unit(s) and that this retentate side stream may be recycled directly to the tank reactor by relying on the pressure differential, ΔP, where $\Delta P = P_{retentate} - P_{reactor}$. Preferably, the synthesis gas remains entrained or dissolved in the suspension as the suspension is passed through the filtration unit. However, the filtration unit(s) may also be operated with a headspace into which entrained or dissolved gases separate from the suspension.

Alternatively, a portion of the withdrawn suspension stream may be recycled to the high shear mixing zone(s) via an external conduit having a first end in communication with the tank reactor and a second end in communication with the high shear mixing zone(s) without being passed through a filtration unit. A mechanical pumping means, for example, a slurry pump and a heat exchanger are arranged on the external conduit. Preferably, the heat exchanger is located downstream of the mechanical pumping means. In this arrangement, a side stream is taken from the withdrawn suspension stream, downstream of the mechanical pumping means, and is passed to at least one filtration unit. The side stream may be taken either upstream or downstream, preferably upstream of the heat exchanger. Where two or more filtration units are employed, the units are preferably arranged in parallel, optionally, with one or more redundant filtration units, as described above. Preferably, the synthesis gas remains entrained or dissolved in the suspension as the suspension is passed through the filtration unit. However, the filtration unit(s) may also be operated with a headspace into which entrained or dissolved gases separate from the suspension. The filtrate stream is withdrawn from the filtration unit(s) and may be passed to product purification and upgrading stages as described in WO 0138269 (PCT patent application number GB 0004444). A retentate stream is withdrawn from the filtration unit(s) and may be recycled through a recycle line to the tank reactor, the withdrawn suspension stream or the suction side of a venturi nozzle. Where the pressure of the retentate stream ($P_{retentate}$) is greater than the pressure in the tank reactor ($P_{reactor}$) or is greater than the pressure in the external conduit upstream of the mechanical pumping means ($P_{conduit}$), the retentate stream may be recycled to the tank reactor or to the external conduit upstream of the mechanical pumping means by relying on the pressure differential, ΔP, where $\Delta P = (P_{retentate} - P_{reactor})$ or $(P_{retentate} - P_{conduit})$ respectively. However, it is also envisaged that the retentate stream may be recycled to the tank reactor or the external conduit via a mechanical pumping means located in the recycle line.

In yet a further arrangement, a first withdrawn suspension stream is recycled to the high shear mixing zone(s) via an external conduit having a first end in communication with the tank reactor, a second end in communication with the high shear mixing zone(s) and a mechanical pumping means located therein. A second withdrawn suspension stream may be passed from the tank reactor to at least one filtration unit via a flow line. Preferably, a mechanical pumping means is omitted from the flow line. Preferably, the synthesis gas remains entrained or dissolved in the suspension as the suspension is passed through the filtration unit. However, the filtration unit(s) may also be operated with a headspace into which entrained or dissolved gases separate from the suspension. Where two or more filtration units are employed, the filtration units are preferably arranged in parallel, optionally, with one or more redundant filtration units, as described above. The filtrate stream is withdrawn from the filtration unit(s) and may be passed to product purification and upgrading stages as described in WO 0138269 (PCT patent application number GB 0004444). In order to maintain turbulent conditions within the filtration unit(s), suspension is withdrawn from at or near the bottom of the filtration unit(s) and is at least in part reintroduced into the filtration unit(s) via a by-pass loop conduit. Where the filtration unit(s) is operated with a headspace, the suspension is reintroduced into the filtration unit(s) at a position below the level of suspension in the filtration unit(s), preferably, immediately below the level of suspension in the filtration unit(s). The suspension is passed around the by-pass loop conduit and through the filtration unit(s) via a mechanical pumping means, for example, a slurry pump located in the by-pass loop conduit. A retentate stream may be taken from the by-pass loop conduit, preferably, downstream of the mechanical pumping means. The retentate stream may be recycled to the tank reactor, the suction side of a venturi nozzle, the high shear mixing zone(s) or the first withdrawn suspension stream through a retentate recycle line. Where $P_{retentate}$ is greater than $P_{reactor}$ or is greater than the pressure in the external conduit upstream of the mechanical pumping means ($P_{conduit}$) the suspension may be recycled to the tank reactor through the retentate recycle line by relying on the pressure differential, ΔP (where $\Delta P = P_{retentate} - P_{reactor}$ or $P_{retentate} - P_{conduit}$). However, it is also envisaged that the retentate stream may be recycled to the tank reactor or the external conduit via a mechanical pumping means located in the retentate recycle line. Where the retentate stream is recycled to the high shear mixing zone(s), it is essential that the recycle line is provided with a mechanical pumping means. Suitably, a heat exchanger is positioned on the retentate recycle line. Where the retentate recycle line is provided with a mechanical pumping means, the heat exchanger may be positioned on the retentate recycle line either upstream or downstream, preferably, upstream of the mechanical pumping means.

Preferably, the total energy input of the mechanical pumping means (located on the external conduit and optionally on the recycle line) is at least 0.5 $kW/m^3$ relative to the total volume of suspension present in the reactor system, more preferably in the range of from 0.5 to 25 $kW/m^3$, most preferably from 0.5 to 10 $kW/m^3$, in particular from 0.5 to 5 $kW/m^3$, for example, from 0.5 to 2.5 $kW/m^3$ relative to the total volume of suspension present in the system.

Suitably, in each of the above arrangements of the filtration unit(s), the withdrawn suspension stream and/or the retentate stream is recycled to the high shear mixing zone(s) at a rate of between 10,000 and 50,000 $m^3$ of suspension per hour, preferably, 15,000 to 30,000 $m^3$ of suspension per hour, more preferably 17,000 to 25,000 $m^3$ of suspension per hour.

Suitably, in each of the above arrangements of the filtration unit(s), the high shear mixing zone(s) may comprise any device suitable for intensive mixing or dispersing of a gaseous stream in a suspension of solids in a liquid medium, for example, a rotor-stator device, an injector-mixing nozzle or a high shear pumping means.

The injector-mixing nozzle(s) can advantageously be executed as a venturi tube (c.f. "Chemical Engineers' Handbook" by J. H. Perry, $3^{rd}$ edition (1953), p. 1285, FIG. 61), preferably an injector mixer (c.f. "Chemical Engineers' Handbook" by J H Perry, $3^{rd}$ edition (1953), p 1203, FIG. 2 and "Chemical Engineers' Handbook" by R H Perry and C H Chilton $5^{th}$ edition (1973) p 6–15, FIGS. 6–31) or most preferably as a liquid-jet ejector (c.f. "Unit Operations" by G G Brown et al, $4^{th}$ edition (1953), p.194, FIG. 210). Alternatively, the injector-mixing nozzle(s) may be executed as a venturi plate. The venturi plate may be positioned transversely within an open ended conduit which discharges suspension containing gas bubbles and/or irregularly shaped gas voids dispersed therein into the tank reactor.

The injector-mixing nozzle(s) may also be executed as a "gas blast" or "gas assist" nozzle where gas expansion is used to drive the nozzle (c.f. "Atomisation and Sprays" by Arthur H Lefebvre, Hemisphere Publishing Corporation, 1989). Where the injector-mixing nozzle(s) is executed as a "gas blast" or "gas assist" nozzle, the suspension of catalyst is fed to the nozzle at a sufficiently high pressure to allow the suspension to pass through the nozzle while the synthesis gas is fed to the nozzle at a sufficiently high pressure to achieve high shear mixing within the nozzle.

The high shear mixing zone(s) of the Fischer-Tropsch synthesis unit may also comprise a high shear pumping means, for example, a paddle or propeller having high shear blades positioned within an open ended conduit which discharges suspension containing gas bubbles and/or irregularly shaped gas voids into the tank reactor. Preferably, the high shear pumping means is located at or near the open end of the conduit. Synthesis gas may be injected into the conduit, for example, via a sparger, located immediately upstream or downstream, preferably immediately upstream of the high shear pumping means.

Preferred arrangements of the high shear mixing zone(s) in the tank reactor are as described in WO 0138269 (PCT patent application number GB 0004444).

In yet a further preferred embodiment of the present invention there is provided a process for converting synthesis gas to hydrocarbons, at least a portion of which are liquid at ambient temperature and pressure, by contacting synthesis gas, at an elevated temperature and pressure, with a suspension comprising a particulate Fischer-Tropsch catalyst suspended in a liquid medium, in a system comprising at least one high shear mixing zone and a tubular loop reactor wherein the process comprises:

a) passing the suspension and synthesis gas through the high shear mixing zone(s) wherein the gaseous stream is broken down into gas bubbles and/or irregularly shaped gas voids;

b) discharging suspension having gas bubbles and/or irregularly shaped gas voids dispersed therein from the high shear mixing zone(s) into the tubular loop reactor;

c) circulating the discharged suspension around the tubular loop reactor under turbulent flow conditions via at least one mechanical pumping means positioned within the tubular loop reactor;

d) withdrawing a suspension stream comprising a portion of the circulating suspension from the tubular loop reactor and feeding the withdrawn suspension stream through at least one filtration unit under turbulent flow conditions via a mechanical pumping means;

e) withdrawing a filtrate stream comprising the liquid medium and liquid hydrocarbons from the filtration unit(s); and f) recycling a retentate stream comprising a concentrated suspension of the particulate Fischer-Tropsch catalyst suspended in the liquid medium and liquid hydrocarbons from the filtration unit(s) to the tubular loop reactor.

In order to simplify the process of this preferred embodiment of the present invention, it is preferred that the liquid medium comprises one of more of the liquid hydrocarbons.

Preferably, the tubular loop reactor is operated without a headspace so as to mitigate the risk of slug flow within the tubular loop reactor.

Preferably, the withdrawn suspension stream is passed from the tubular loop reactor to at least one filtration zone via a flow line. Preferably, a mechanical pumping means is omitted from the flow line. Preferably, the synthesis gas remains entrained or dissolved in the suspension as the suspension is passed through the filtration unit. However, the filtration unit(s) may also be operated with a headspace into which entrained or dissolved gases separate from the suspension. Where two or more filtration units are employed, the filtration units are preferably arranged in parallel, optionally, with one or more redundant filtration units, as described above. The filtrate stream is withdrawn from the filtration unit(s) as described above. In order to maintain turbulent conditions within the filtration unit(s), suspension is withdrawn from at or near the bottom of the filtration unit(s) and is at least in part reintroduced into the filtration unit(s) via a by-pass loop conduit. Where the filtration unit(s) is operated with a headspace, the suspension is reintroduced at a position below the level of suspension in the filtration unit(s), preferably, immediately below the level of suspension in the filtration unit(s). The suspension is passed around the by-pass loop conduit and through the filtration unit(s) via a mechanical pumping means, for example, a slurry pump located in the by-pass loop conduit. A retentate stream may be taken from the by-pass loop conduit, preferably downstream of the mechanical pumping means. The retentate stream may be recycled to the tubular loop reactor through a retentate recycle line. Where $P_{retentate}$ is greater than $P_{reactor}$, the retentate stream may be recycled to the tubular loop reactor by relying on the pressure differential, $\Delta P$ (where $\Delta P = P_{retentate} - P_{reactor}$). However, where necessary, a mechanical pumping means may be located in the recycle line. Optionally, a heat exchanger may be positioned on the retentate recycle line.

The high shear mixing zone(s) may be an injector-mixing nozzle of the types described above, which discharge their contents into the tubular loop reactor. The injector-mixing nozzle(s) may project through the walls of the tubular loop reactor in which case it may be necessary to recycle suspension from the tubular loop reactor to the injector mixing nozzle(s) via a slurry line(s). Suitably, the suspension may be circulated through the tubular loop reactor via at least one mechanical pumping means, for example, a paddle or propeller positioned therein. Preferably, a plurality of injector-mixing nozzles are spaced apart along the length of the tubular loop reactor. Preferably, a plurality of mechanical pumping means are spaced apart along the length of the tubular loop conduit.

The tubular loop reactor may also have at least one internal high shear mixing zone. Preferably, a plurality of such internal high shear mixing zones are spaced apart along the length of the tubular loop reactor. The internal high shear mixing zone(s) may comprise a section of the tubular loop reactor containing a high shear pumping means, for example, a paddle or propeller having high shear blades. Synthesis gas is introduced into this section of the tubular loop conduit, for example, via gas sparger. Preferably, the gas sparger is located in the section of tubular loop conduit either immediately upstream or downstream, preferably immediately upstream of the high shear pumping means. Without wishing to be bound by any theory, the injected synthesis gas is believed to be broken down into gas bubbles and/or irregularly shaped gas voids by the fluid shear imparted to the suspension by the high shear pumping means. It is also envisaged that the internal high shear mixing zone(s) may comprise a section of the tubular loop reactor containing an injector-mixing nozzle, in particular a venturi plate. Synthesis gas is introduced into the section of the tubular loop reactor, for example, via a gas sparger, which is preferably located immediately downstream of the venturi plate. In this arrangement, it will be necessary to circulate the suspension around the tubular loop reactor via at least one mechanical pumping means.

Suitably, the total power input of the mechanical pumping means is equivalent to an energy dissipation rate of at least 0.5 $kW/m^3$, preferably 0.5 to 25 $kW/m^3$, more preferably 0.5 to 10 $kW/m^3$, most preferably 0.5 to 2.5 $kW/m^3$ based on the total volume of suspension in the reactor system. Preferably, the suspension is circulated around the tubular loop reactor at a flow rate of between 10,000 $m^3$ per hour and 50,000 $m^3$ per hour. Suitably, suspension is withdrawn from the tubular loop reactor immediately downstream of a mechanical pumping means.

The contents of the tubular loop reactor may be cooled by means of an external heat exchanger which is disposed along part or substantially along the entire length of the tubular loop reactor. It is also envisaged that an internal heat exchanger, for example, cooling coils, tubes or plates may be located within the tubular loop reactor, for example, in one or more sections of the tubular loop reactor.

Preferably, the hydrocarbons comprise a mixture of hydrocarbons having a chain length of greater than 5 carbon atoms. Suitably, the hydrocarbons comprise a mixture of hydrocarbons having chain lengths of from 5 to about 90 carbon atoms (which are liquid under the process conditions). Preferably, a major amount, for example, greater than 60% by weight, of the hydrocarbons have chain lengths of from 5 to 30 carbon atoms. Suitably, the liquid medium comprises one or more of the higher hydrocarbons.

The catalyst which may be employed in the process of the present invention is any catalyst known to be active in Fischer-Tropsch synthesis. For example, Group VIII metals whether supported or unsupported are known Fischer-Tropsch catalysts. Of these iron, cobalt and ruthenium are preferred, particularly iron and cobalt, most particularly cobalt.

A preferred catalyst is supported on carbon based support, for example, graphite or an inorganic oxide support, preferably a refractory inorganic oxide support. Preferred supports include silica, alumina, silica-alumina, the Group IVB oxides, titania (primarily in the rutile form) and most preferably zinc oxide. The support generally has a surface area of less than about 100 $m^2/g$, but may have a surface area of less than 50 $m^2/g$ or less than 25 $m^2/g$, for example, about 5 $m^2/g$.

The catalytic metal is present in catalytically active amounts usually about 1–100 wt %, the upper limit being attained in the case of unsupported metal catalysts, preferably 2–40 wt %. Promoters may be added to the catalyst and are well known in the Fischer-Tropsch catalyst art. Promoters can include ruthenium, platinum or palladium (when not the primary catalyst metal), aluminium, rhenium, hafnium, cerium, lanthanum and zirconium, and are usually present in amounts less than the primary catalytic metal (except for ruthenium which may be present in coequal amounts), but the promoter:metal ratio should be at least 1:10. Preferred promoters are rhenium and hafnium.

Suitably, the Fischer-Tropsch catalyst has a particle size in the range 1 micron to 3 mm, preferably 5 microns to 1 mm, more preferably in the range 5 to 500 microns, most preferably 10 to 250 microns, for example 20 to 50 microns.

Preferably, the suspension of catalyst which is present in the reactor (for example, a tank reactor or tubular loop reactor) comprises less than 40% wt of catalyst particles, more preferably 10 to 30% wt of catalyst particles, most preferably 10 to 20% wt of catalyst particles.

The process of the present invention may be operated in batch or continuous mode, the latter being preferred.

In a continuous process, the filtrate stream is continuously passed to a product purification stage where water by-product may be removed from the liquid hydrocarbons and any liquid medium. As discussed above, the retentate stream may be recycled either directly or indirectly to the reactor vessel tank reactor or tubular loop reactor). Fresh catalyst may be added either to the recycled concentrated slurry or directly into the reactor vessel.

The liquid hydrocarbon products from the purification stage may be fed to a hydrocracking stage as described in PCT patent application number GB 0004444.

BRIEF DESCRIPTION OF THE DRAWINGS

The process of the present invention will now be illustrated by reference to the accompanying figures, in which.

DETAILED DESCRIPTION OF PREFERRED EMBODIMENTS

Figure 1:
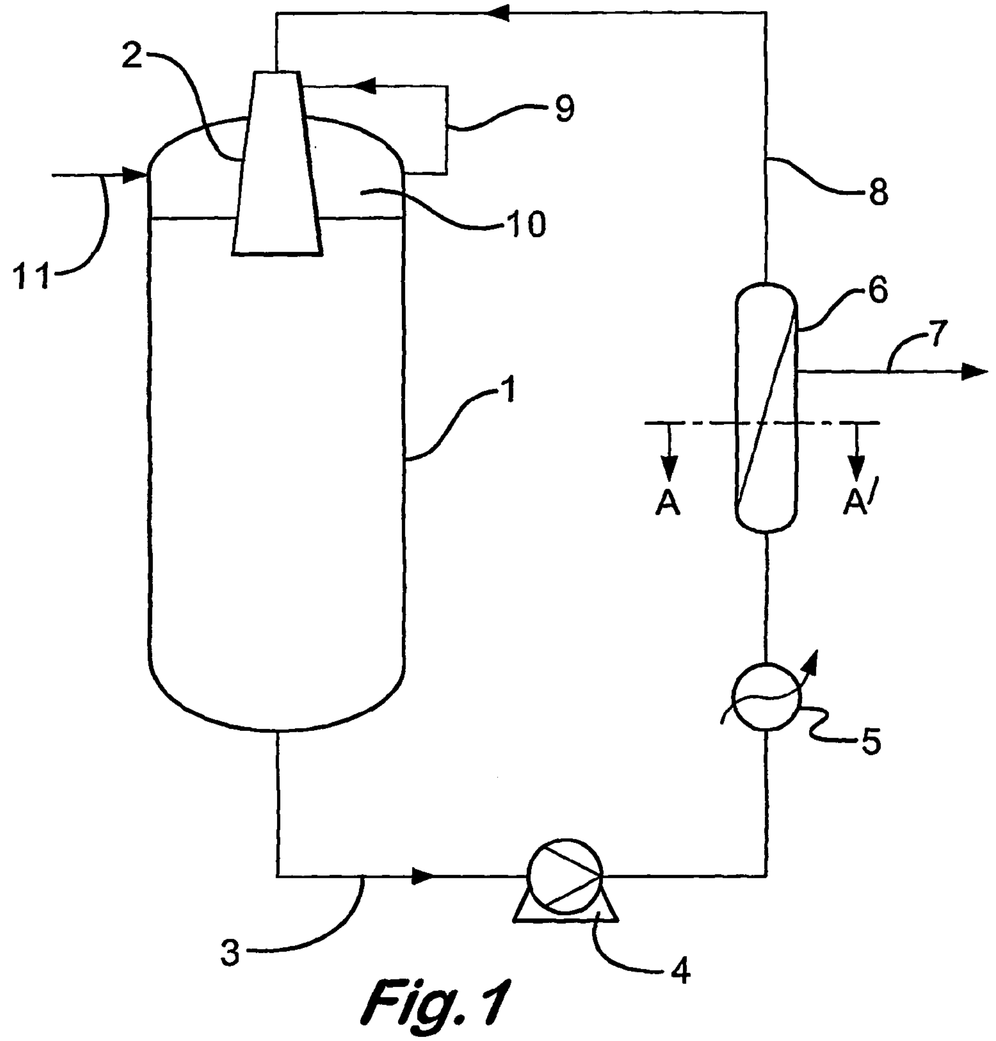
FIG. 1 is a schematic of an apparatus for carrying out the process of the present invention.

In FIG. 1, a suspension stream comprising particulate Fischer-Tropsch catalyst suspended in liquid hydrocarbon products is withdrawn from a tank reactor (1) and is recycled to an injector mixing nozzle (2) through an external conduit (3) via a mechanical pumping means (4). A heat exchanger (5) and a filtration unit (6) is positioned on the external conduit (3) downstream of the mechanical pumping means (4). The filtration unit (6) comprises a plurality of hollow cylindrical filter elements (not shown). A filtrate stream (7) comprising liquid hydrocarbons permeates through the hollow cylindrical filter elements and is removed from the filtration unit (6) and is passed to a product purification stage (not shown). A retentate stream (8) comprising a concentrated slurry of particulate Fischer-Tropsch catalyst in the liquid hydrocarbons is retained by the filter elements and is recycled to the injector mixing nozzle (2) through the external conduit (3). A gaseous stream (9) comprising unreacted synthesis gas is withdrawn from the headspace (10) of the tank reactor and is recycled to the injector-mixing nozzle (2). Fresh synthesis gas may be introduced to the gaseous recycle stream via line (11).

Figure 2:
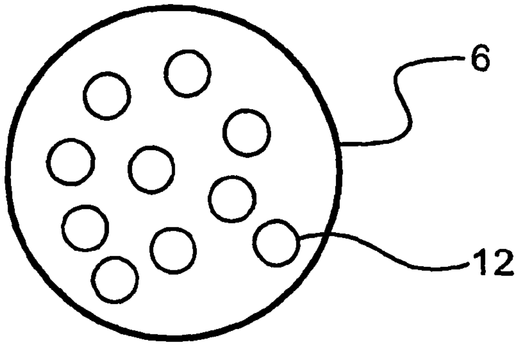
FIG. 2 is a cross section of a filtration unit along line A A' in FIG. 1.

FIG. 2 shows a cross-section through the filtration unit (6) along line AA'. The filtration unit contains a plurality of hollow cylindrical filter elements (12) which are aligned with the longitudinal axis of the filtration unit (6). The hollow cylindrical filter elements (12) are formed from a porous material having a pore size which is small enough to retain the smallest of the catalyst particles. A filtrate stream is removed from the interior of the hollow cylindrical filter elements (12).

Figure 3:
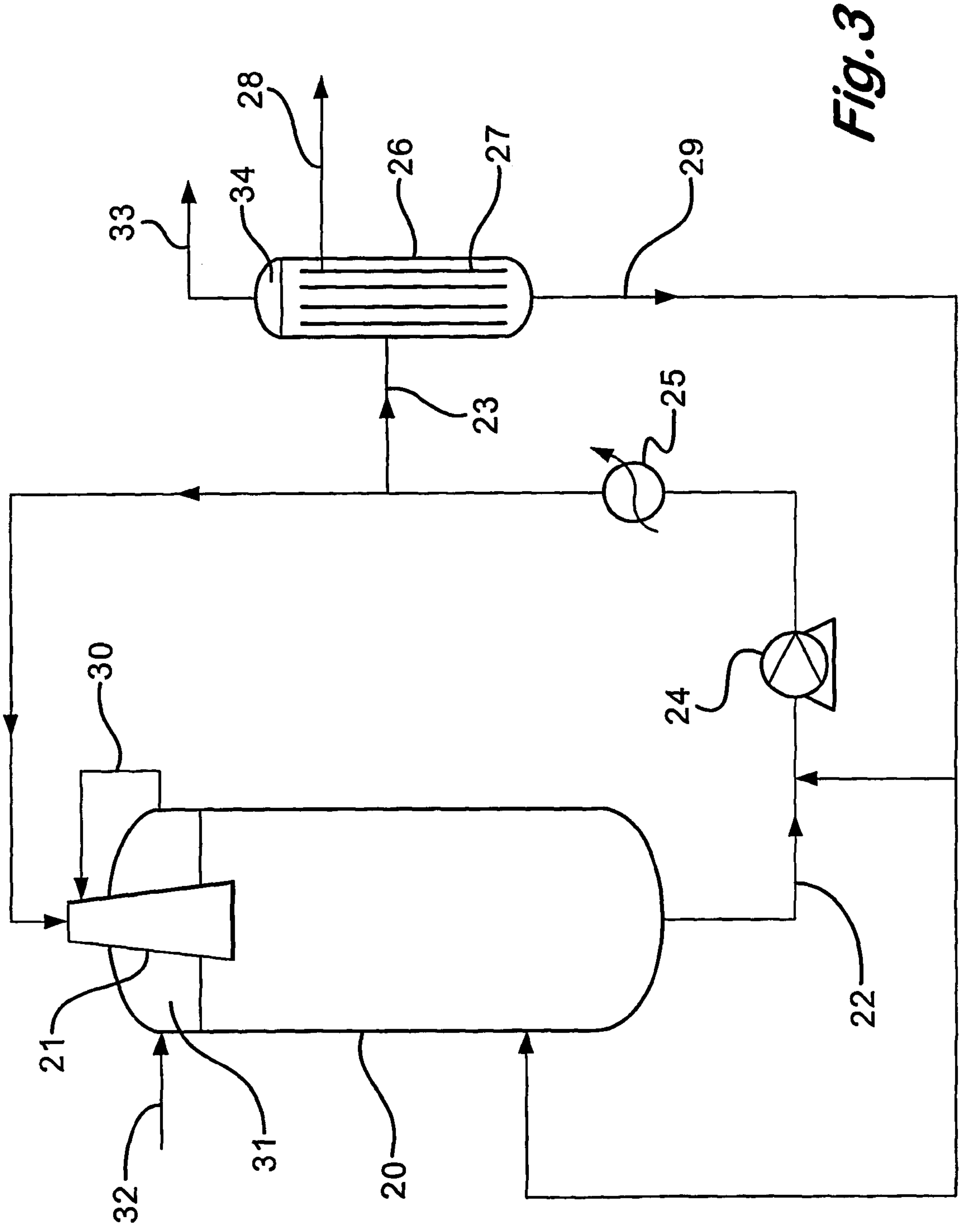
FIG. 3 is a schematic of another apparatus for carrying out the process of the present invention.

In FIG. 3, a suspension stream comprising particulate Fischer-Tropsch catalyst suspended in liquid hydrocarbons is withdrawn from a tank reactor (20) and is, in part, recycled to an injector mixing nozzle (21) through an external conduit (22). A suspension side stream (23) is removed from the external conduit downstream of a mechanical pumping means (24) and a heat exchanger (25). The suspension side stream (23) is fed to a filtration unit (26) comprising a plurality of hollow cylindrical filter elements (27). A filtrate comprising liquid hydrocarbons permeates through the filter elements and a filtrate stream is removed from the filtration unit (26) through line (28) and is passed to a product purification stage (not shown). A retentate comprising a concentrated slurry of particulate Fischer-Tropsch catalyst in the liquid hydrocarbons is retained by the filter elements (27). Where $P_{retentate}$ is greater than $P_{reactor}$, a retentate stream may be recycled directly to the tank reactor (20) via recycle line (29). Alternatively, the retentate stream may be recycled to the external conduit (22) upstream of the mechanical pumping means (24) or to the suction side of a venturi nozzle (not shown). A gaseous stream (30) comprising unreacted synthesis gas is withdrawn from the headspace (31) of the tank reactor and is recycled to the injector-mixing nozzle (21). Fresh synthesis gas may be introduced to the gaseous recycle stream via line (32). It is also envisaged that a gaseous stream (33) may be withdrawn from the headspace (34) of filtration unit (26) and may be recycled to the tank reactor (20) or to the injector-mixing nozzle (21) (not shown).

Figure 4:
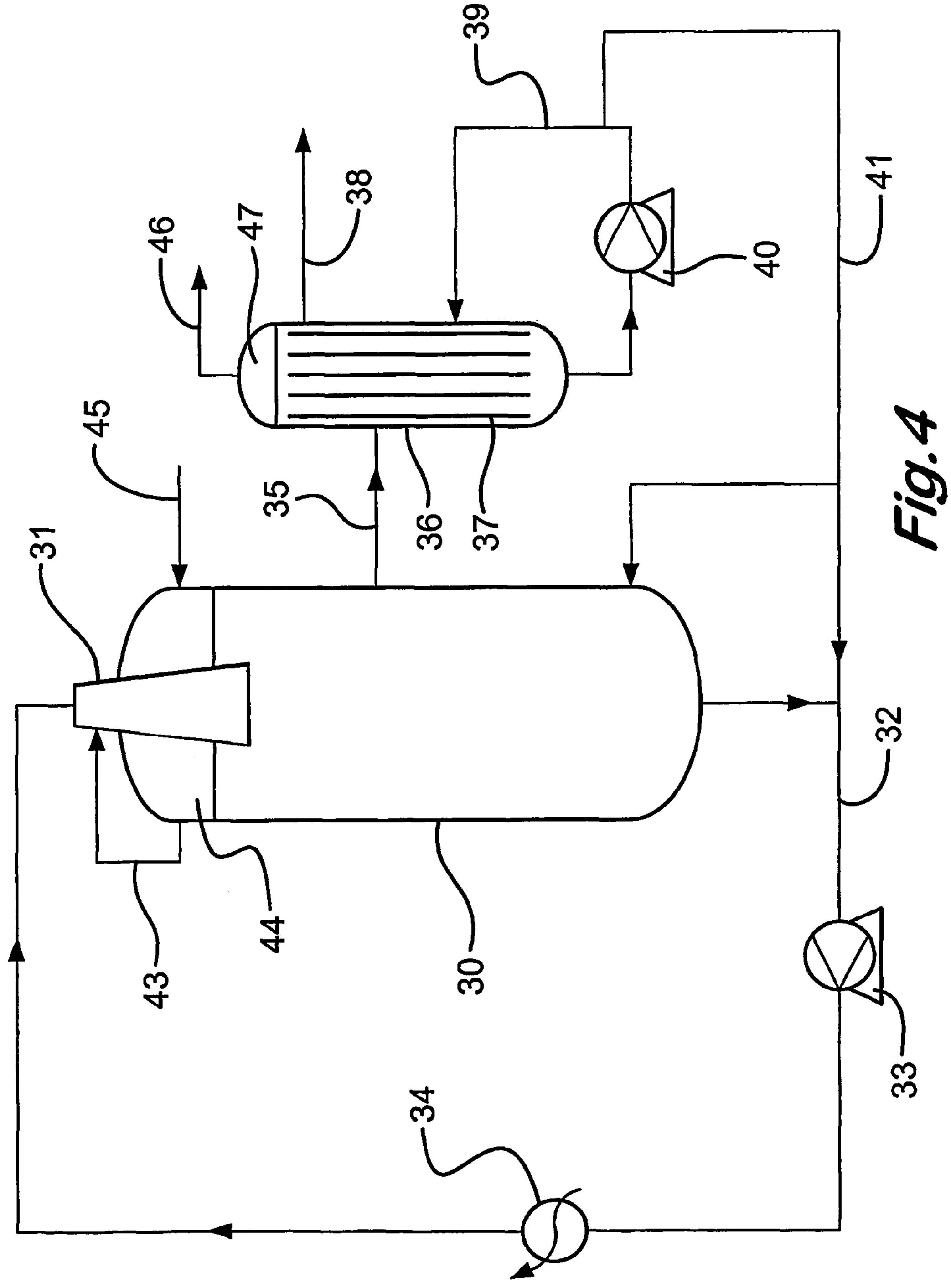
FIG. 4 is schematic of a further apparatus for carrying out the process of the present invention.

In FIG. 4, a first suspension stream comprising particulate Fischer-Tropsch catalyst suspended in liquid hydrocarbons is withdrawn from a tank reactor (30) and is recycled to an injector mixing nozzle (31) through an external conduit (32) via a mechanical pumping means (33). A heat exchanger (34) is positioned on the external conduit (32). A second suspension stream comprising particulate Fischer-Tropsch catalyst suspended in liquid hydrocarbons is withdrawn from the tank reactor (30) via line (35) and is introduced into a filtration unit (36). The filtration unit comprises a plurality of hollow cylindrical filter elements (37). A filtrate stream comprising liquid hydrocarbon products permeates through the filter elements (37) and a filtrate stream is removed from the filtration unit (36) via line (38) and is passed to a product purification stage (not shown). Suspension is removed from at or near the bottom of the filtration unit (36) and is recycled to the filtration unit (36) via a by-pass loop conduit (39) having a mechanical pumping means (40) positioned therein. A retentate stream comprising a concentrated slurry of particulate Fischer-Tropsch catalyst in the liquid hydrocarbon products is removed from the by-pass loop conduit (39) downstream of the mechanical pumping means (40) and, where $P_{retentate}$ is greater than $P_{reactor}$, may be recycled directly to the tank reactor (30) via recycle line (41). Alternatively, the retentate stream may be recycled to the suction side of a venturi nozzle (not shown). It is also envisaged that the retentate stream may be recycled to the external conduit (32) upstream of the mechanical pumping means (33) via recycle line (42). A gaseous stream (43) comprising unreacted synthesis gas is withdrawn from the headspace (44) of the tank reactor (30) and is recycled to the injector-mixing nozzle (31). Fresh synthesis gas may be introduced to the gaseous recycle stream via line (45). It is also envisaged that a gaseous stream (46) may be withdrawn from the headspace (47) of the filtration unit (36) and may be recycled to the tank reactor (30) or to the injector-mixing nozzle (31) (not shown).

Figure 5:
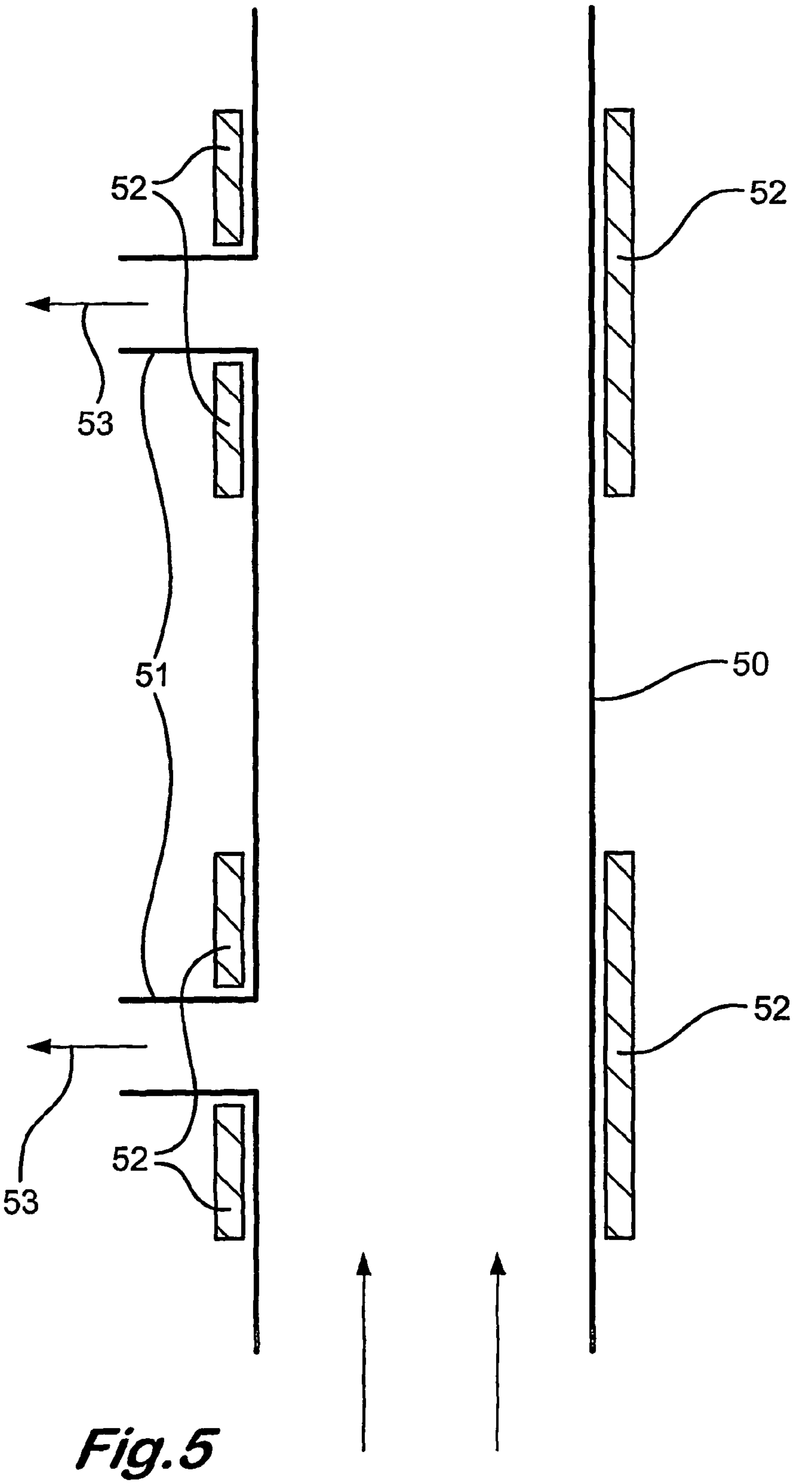
FIG. 5 shows a T-piece magnetic separator.

FIG. 5 illustrates a T-piece magnetic separator. Suspension is passed through a main conduit (50) of the T-piece separator. The main conduit (50) has branch conduits (51) and is provided with magnetic devices (52). As the suspension is passed through the main conduit (50) side streams (53) having a reduced content of particulate Fischer-Tropsch catalyst are removed via the branch conduits (51). The magnetic devices (52) assist is retaining the particulate Fischer-Tropsch catalyst within the main conduit of the T-piece separator since conventional particulate Fischer-Tropsch catalysts comprising iron, cobalt or ruthenium are magnetic.

The invention claimed is:

1. Process for converting synthesis gas to hydrocarbons which comprises contacting a gaseous stream comprising synthesis gas, at an elevated temperature and pressure, with a suspension comprising a particulate Fischer-Tropsch catalyst having a particle size in the range 5 microns to 500 microns, suspended in a liquid medium, in a system comprising at least one high shear mixing zone and a reactor vessel wherein the process comprises:

passing the suspension and the gaseous stream through the high shear mixing zone(s) wherein the gaseous stream is broken down into gas bubbles;

discharging suspension having gas bubbles dispersed therein from the high shear mixing zone(s) into the reactor vessel; and withdrawing suspension comprising the particulate Fischer-Tropsch catalyst suspended in the liquid medium and liquid hydrocarbon products from the reactor vessel and recycling at least a portion of the suspension to the high shear mixing zone(s) via an external conduit at a flow rate of at least 10,000 $m^3$ of suspension per hour; and taking a side stream from the suspension flowing through the external conduit and passing the side stream directly to a filtration unit.

2. Process according to claim 1 wherein a pumping means is positioned on the external conduit.

3. Process according to claim 1 wherein the suspension flows through the external conduit at a rate of between 10,000 and 50,000 $m^3$ of suspension per hour.

4. Process according to claim 2 wherein the suspension side stream which is passed directly to the filtration unit is withdrawn from the external conduit downstream of the pumping means.

5. Process according to claim 1 wherein the suspension which is passed through the external conduit is cooled by means of an external heat exchanger.

6. Process for converting synthesis gas to hydrocarbons by contacting a gaseous reactant stream comprising synthesis gas, at an elevated temperature and pressure, with a suspension comprising a particulate Fischer-Tropsch catalyst having a particle size in the range 5 to 500 microns suspended in a liquid medium, in a system comprising at least one high shear mixing zone and a tubular loop reactor wherein the process comprises:

passing the suspension and the gaseous stream through the high shear mixing zone(s) wherein the gaseous stream is broken down into gas bubbles;

discharging suspension having gas bubbles dispersed therein from the high shear mixing zone(s) into the tubular loop reactor;

circulating the discharged suspension around the tubular loop reactor at a flow rate of at least 10,000 $m^3$ of suspension per hour;

withdrawing a product suspension stream comprising at least a portion of the circulating suspension from the tubular loop reactor and feeding at least a portion of the product suspension stream directly to a filtration unit.

7. Process according to claim 6 wherein the tubular loop reactor has a pumping means positioned therein.

8. Process according to claim 6 wherein the suspension is circulated around the tubular loop reactor at a flow rate of between 10,000 $m^3$ per hour and 50,000 $m^3$ per hour.

9. Process according to claim 6 wherein the product suspension is withdrawn from the tubular loop conduit immediately downstream of the pumping means and then at least a portion of the product suspension stream is introduced directly to the filtration unit.

10. Process according to claim 1 wherein the product suspension stream which is fed to the filtration unit is separated into at least a portion which permeates through the filter (the "filtrate") and another portion which is retained by the filter (the "retentate").

11. Process according to claim 1 wherein the pressure differential across the filtration unit is in the range of 0.5 to 30 bar.

12. Process according to claim 1 wherein the flow rate of product suspension along the filtration unit is at least 1 $ms^{-1}$.

13. Process according to claim 1 wherein the flux (volume of liquid hydrocarbon products and any liquid medium permeating through the filtration unit per hour through 1 $m^2$ of filtration area) is at least 80 $l/m^2/h$.

14. Process according to claim 1 wherein the ratio of the amount of liquid which permeates through the filter (filtrate) to the amount of liquid which is retained in the retentate is in the range 0.1:100 to 60:100.

15. Process according to claim 1 wherein the concentrated suspension comprises at least 50% wt of catalyst particles.

16. Process according to claim 1 wherein the retentate is recycled from the filtration unit to the reaction zone in the form of a concentrated slurry.

17. Process according to claim 1 wherein the retentate slurry is recycled to the reaction zone via a slurry pump.

18. Process according to claim 1 wherein the retentate slurry is recycled to the reaction zone via a slurry pump and a heat exchanger.

* * * * *